US008084741B2

(12) United States Patent
Gagnon et al.

(10) Patent No.: US 8,084,741 B2
(45) Date of Patent: Dec. 27, 2011

(54) CONFIGURABLE COINCIDENCE PAIRING AND FILTERING SYSTEM AND METHOD FOR POSITRON EMISSION TOMOGRAPHY

(75) Inventors: Daniel Gagnon, Twinsburg, OH (US); Ognian Ivanov, Lake Zurich, IL (US); Barry Roberts, Gurnee, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/571,562

(22) Filed: Oct. 1, 2009

(65) Prior Publication Data

US 2011/0079723 A1 Apr. 7, 2011

(51) Int. Cl.
*G01T 1/20* (2006.01)
(52) U.S. Cl. ........................................ 250/362
(58) Field of Classification Search .................. 250/362, 250/370.01–370.15; 378/98.8
See application file for complete search history.

(56) References Cited

U.S. PATENT DOCUMENTS

| | | | |
|---|---|---|---|
| 2009/0242776 A1* | 10/2009 | Kobashi et al. | 250/363.04 |
| 2010/0078569 A1* | 4/2010 | Jarron et al. | 250/363.04 |
| 2010/0193697 A1* | 8/2010 | Bal et al. | 250/370.09 |

OTHER PUBLICATIONS

Beuther et al., "List mode-driven cardiac and respiratory gating in PET," May 2009, The Journal of Nuclear Medicine, vol. 50, No. 5, pp. 674-681.*
Li et al., "A HOTLink/Networked PC data acquisition and image reconstruction system for a high-resolution whole-body PET with respiratory or ECG-gated performance," 2003, IEEE Transactions on Nuclear Sciences, vol. 50, No. 3, pp. 393-397.*
Kesner et al., "Respiratory gated PET derived from raw PET data," 2007, IEEE Nuclear Science Symposium Conference Record, pp. 2686-2691.*
M.-A. Tetrault, et al., Real Time Coincidence detection Engine for High Count Rate Timestamp Based PET, IEEE Transactions on Nuclear Science, vol. 57. No. 1, Feb. 2010, p. 117-124.

* cited by examiner

Primary Examiner — Kiho Kim
(74) Attorney, Agent, or Firm — Oblon, Spivak, McClelland, Maier & Neustadt, L.L.P.

(57) ABSTRACT

A method of processing positron emission tomography (PET) information obtained from a PET detector having a plurality of detector regions, each detector region having at least one detector module and a corresponding regional collector, the method including the steps of receiving PET event information for a single PET event, the PET event information including energy information and crystal position information of the single PET event; receiving non-detector event information; generating an event list that includes (1) a PET event entry, the PET event entry including a fine time stamp, the energy information, and the crystal position information, and (2) a non-detector event entry that includes the received non-detector event information; and transmitting the generated event list to a computer for off-line processing.

21 Claims, 6 Drawing Sheets

List Format for Single Events

Single Event – data format (one entry in the list for each event)

| Energy [9-bits] | Crystal Position [18-bits] | Fine Time Stamp [20-bits] | Entry Type |
|---|---|---|---|

Coarse Time Stamp – data format (one entry in the list every 25.6uS)

| Coarse Time Stamp [32-bits] | Entry Type |
|---|---|

Global Time Stamp – can be compiled from the list for each event (supports up to 30 hours scan)

| Coarse Time Stamp [32-bits] | Fine Time Stamp [20-bits] |
|---|---|

FIG. 2

CONFIGURABLE COINCIDENCE PAIRING AND FILTERING SYSTEM AND METHOD FOR POSITRON EMISSION TOMOGRAPHY

BACKGROUND OF THE INVENTION

1. Field of the Invention

This invention generally relates to a positron emission tomography (PET) imaging system, more specifically, to pairing and filtering detection events for energy, timing, and spatial characteristics.

2. Discussion of the Background

The use of positron emission tomography (PET) is growing in the field of medical imaging. In PET imaging, a radiopharmaceutical agent is introduced into the object to be imaged via injection, inhalation, or ingestion. After administration of the radiopharmaceutical, the physical and bio-molecular properties of the agent will cause it to concentrate at specific locations in the human body. The actual spatial distribution of the agent, the intensity of the region of accumulation of the agent, and the kinetics of the process from administration to eventually elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time, an annihilation event produces two gamma rays at 511 keV traveling at substantially 180 degrees apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line. Limitations in the timing resolution of the scanner will determine the accuracy of the positioning along this line. Limitations in the determination of the location of the original scintillation events will determine the ultimate spatial resolution of the scanner, while the specific characteristics of the isotope (e.g., energy of the positron) will also contribute (via positron range and co-linearity of the two gamma rays) to the determination of the spatial resolution the specific agent.

The collection of a large number of events creates the necessary information for an image of an object to be estimated through tomographic reconstruction. Two detected events occurring at substantially the same time at corresponding detector elements form a line-of-response that can be histogrammed according to their geometric attributes to define projections, or sinograms to be reconstructed. Events can also be added to the image individually.

The fundamental element of the data collection and image reconstruction is therefore the LOR, which is the line traversing the system-patient aperture. Additional information can be obtained regarding the location of the event. First, it is known that, through sampling and reconstruction, the ability of the system to reconstruct or position a point is not space-invariant across the field of view, but is better in the center, slowly degrading toward the periphery. A point-spread-function (PSF) is typically used to characterize this behavior. Tools have been developed to incorporate the PSF into the reconstruction process. Second, the time-of-flight, or time differential between the arrival of the gamma ray on each detector involved in the detection of the pair, can be used to determine where along the LOR the event is more likely to have occurred.

The above described detection process must be repeated for a large number of annihilation events. While each imaging case must be analyzed to determine how many counts (i.e., paired events) are required to support the imaging task, current practice dictates that a typical 100-cm long, FDG (fluorodeoxyglucose) study will need to accumulate several hundred million counts. The time required to accumulate this number of counts is determined by the injected dose of the agent and the sensitivity and counting capacity of the scanner.

PET imaging systems use detectors positioned across from one another to detect the gamma rays emitting from the object. Typically a ring of detectors is used in order to detect gamma rays coming from each angle. Thus, a PET scanner is typically substantially cylindrical to be able to capture as much radiation as possible, which should be, by definition, isotropic. The use of partial rings and rotation of the detector to capture missing angles is also possible, but these approaches have severe consequences for the overall sensitivity of the scanner. In a cylindrical geometry, in which all gamma rays included in a plane have a chance to interact with the detector, an increase in the axial dimension has a very beneficial effect on the sensitivity or ability to capture the radiation. Thus, the best design is that of a sphere, in which all gamma rays have the opportunity to be detected. Of course, for application to humans, the spherical design would have to be very large and thus very expensive. Accordingly, a cylindrical geometry, with the axial extent of the detector being a variable, is realistically the starting point of the design of a modern PET scanner.

While a PET detector can only detect single interactions, i.e., one gamma ray interacting with a crystal and generating light through a scintillation process, PET events are defined by two of those detections occurring at substantially the same time or in coincidence, at substantially 511 keV, and in a geometry compatible with the annihilation event to have occurred in an object of interest. It is therefore required for a PET system to properly identify the timeline for each event in order to correctly match or pair events. This is typically accomplished by constructing a complex network of real-time comparators. As the requirement for count rate is also very demanding (up to hundreds of millions of single events per second), the construction of the coincidence circuitry also needs to handle a very large numbers of counts.

Because of the high demand on efficiency, i.e., being able to receive and process hundreds of millions of events per second, the design of the coincidence circuitry is typically one of the most important elements of the PET detection system. Trigger lines are typically brought to centralized hardware for comparison. Usually the coincidence window, or the period of time within which two events will be deemed to be "at the same time," is set from high-level system controls and does not typically vary during a study or even between studies.

Conventional PET systems suffer from several disadvantages and limitations. For example, conventional systems are very complex since the number of possible coincidences that can originate from independent detectors increases exponentially. While this complexity is manageable when trigger signals come from a few dozens or even a few hundreds of detector elements, it can become simply intractable with pixelated systems that can count several thousand independent signals.

Further, conventional PET systems are also rigid and allow for very little variation in the bandwidth, geometry, and filtering parameters. In addition, coincidence circuitry in conventional systems is typically destructive in the sense that the very action of pairing events destroys the timing information, and a variable coincidence window cannot be applied on the same data.

SUMMARY OF THE INVENTION

Exemplary embodiments of the present invention are directed to a PET system in which a detection events are tagged with an appropriate time stamp and sent to an off-line processing system, allowing for (1) more flexibility in how the data sources (detectors) are connected; (2) more flexibility in allocating processing resources; and (3) more flexibility in what processing/filtering is actually performed on the data.

In particular, one embodiment of the present invention is directed to a system for collecting and processing positron emission tomography (PET) information, comprising: a plurality of detector modules arranged in a plurality of detector regions; a plurality of regional event collectors corresponding to the plurality of detector regions, each regional event collector configured to receive PET event information from each detector module in the corresponding detector region; and a global event collector configured to receive (1) the PET event information from each of the plurality of regional event collectors, the PET event information including energy information and crystal position information of a single PET event, and (2) non-detector event information, the global event collector further configured to generate an event list that includes (i) a PET event entry, the PET event entry including a fine time stamp, the energy information, and the crystal position information, and (ii) a non-detector event entry that includes the received non-detector event information, and to transmit the generated event list to a computer for off-line processing.

Another embodiment of the present invention is directed to a method of processing positron emission tomography (PET) information obtained from a PET detector having a plurality of detector regions, each detector region having at least one detector module and a corresponding regional collector, the method comprising: receiving PET event information for a single PET event, the PET event information including energy information and crystal position information of the single PET event; receiving non-detector event information; generating an event list that includes (1) a PET event entry, the PET event entry including a fine time stamp, the energy information, and the crystal position information, and (2) a non-detector event entry that includes the received non-detector event information; and transmitting the generated event list to a computer for off-line processing.

According to one aspect of the present invention, the generating step comprises generating the event list, the event list including coarse time stamp entries at regular, periodic positions within the event list.

According to another aspect of the present invention, the generating step comprises generating the event list that includes the PET event entry, the PET event entry including an entry type.

According to still another aspect of the present invention, the step of receiving non-detector event information comprises receiving the non-detector event information including at least one of bed location information, angular position of a detector, cardiac EKG information, respiratory gating signal information, events from another detector, and other physiological information.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 illustrates a format of a single event, coarse time stamp, and global time stamp;

DETAILED DESCRIPTION OF THE PREFERRED EMBODIMENTS

Figure 3:
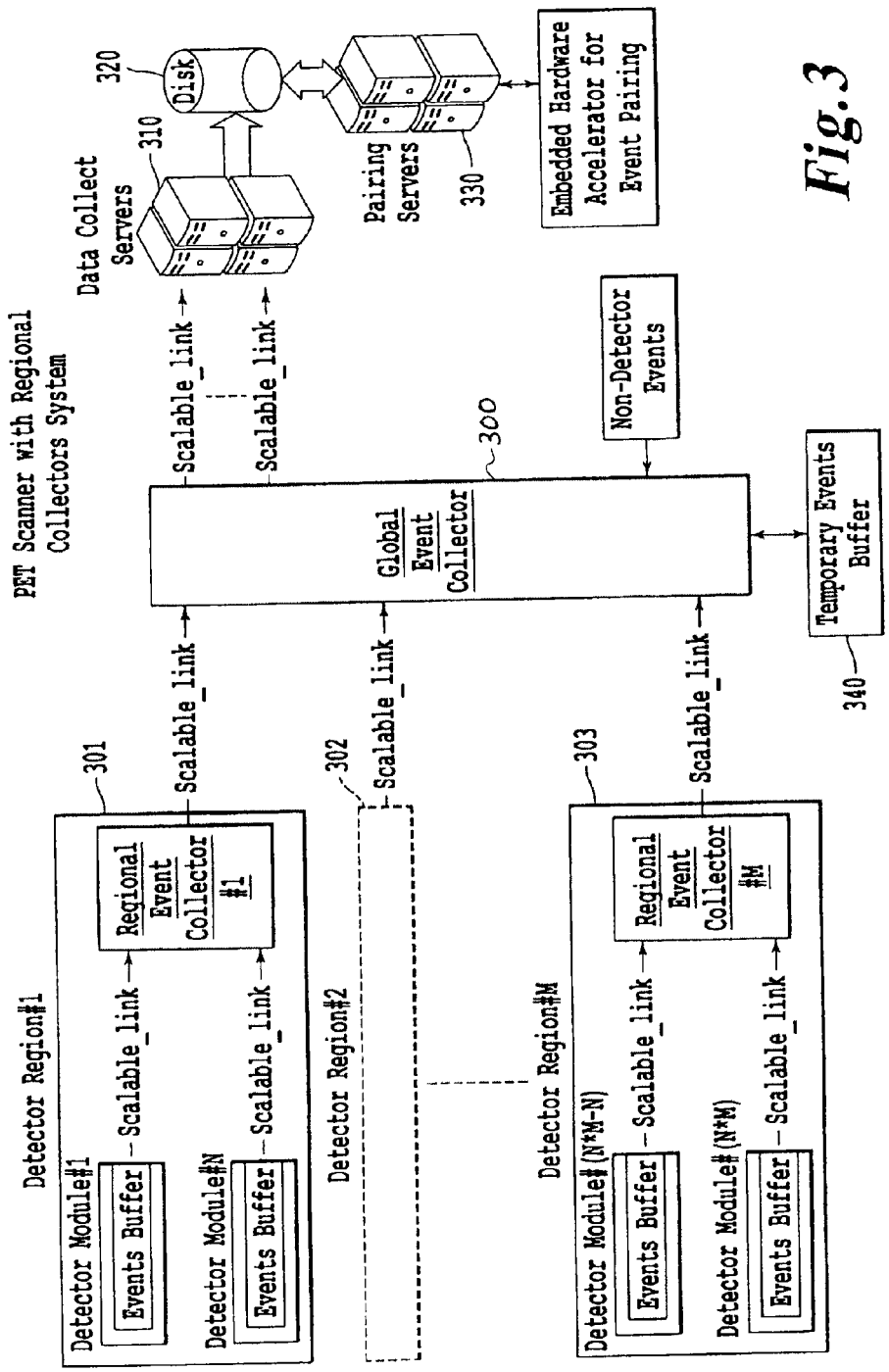
FIG. 3 illustrates a system according to an embodiment of the present invention.

As shown in FIG. 3, one aspect of the design of an embodiment of the present invention is the directing of a subset of all the events to a global event collector board, where analysis of the events can be started. In fact, depending on the count rate (or the overall randoms fraction), the selection of the detector elements feeding a collector can help optimize the filtering operation. For instance, at a higher count rate, it is more efficient to gather events from contiguous detectors as, by definition, no true coincidence can originate from them. In those cases, the global event collector would simple and automatically discard coincidence events from this spatial neighborhood so as to decrease the necessary acquisition bandwidth. However, proper recording and reporting of the actual rate may be necessary to perform a complete randoms correction. In cases of low-to-moderate count rate, the global event collector is connected to a subset of detector elements uniformly covering the entire range so as to improve the chance of finding true pairs and preparing (sorting) the data more effectively for subsequent phases.

In FIG. 3, the global event collector 300 receives event information from regional collector 301, which include N detector modules connected to a regional event collector. The regional collectors have a similar architecture. As shown in FIG. 3, the global event collector 300 also receives non-detector events, which includes information regarding the bed position, gantry rotation, and other standard laboratory timing reference information. The global event collector associates in time the detector information received by the regional collectors 301-303 with the corresponding non-detector events information, such as the bed and gantry positions.

As shown in FIG. 3, the information collected by the global event collector is sent to data collect servers 310 for storage in an associated database/disk storage 320. Event pairing is performed by pairing servers 330, which access the information stored in the database 320. Alternatively, the data collect servers 310 and the pairing servers can be implemented by the same machine.

As shown in FIG. 3, the global event collector 300 combines event data from all detectors into a single list. The format of the event list is described in more detail below with respect to FIGS. 1 and 2.

The global event also incorporates non-detector events into the event list, such as those events related to the motion/position of the patient bed and the detector ring, and physiological information such as EKG information. The non-detector events occur on a different time scale and describe, e.g., the position of the patient bed as a function of time, the angular position on the PET detector ring as a function of time, an EKG signal, a respiratory signal trace, and any other physiological or transducer signal necessary to perform the final reconstruction and presentation of the PET event data.

In creating the event list, the global event collector 300 must reorder the events to arrange the events in chronological order. Further, the global event collector 300 must buffer temporary event bursts into a temporary events buffer for later processing. In the case of a buffer overflow condition, the global event collector will randomly discard received events.

Another function that can be performed by the global event collector is in-line event filtering to discard events from the event list with data information (e.g., energy) outside of a window of interest. The window of interest or other filtering criteria is programmable.

In an alternative embodiment, some of the non-detector events are arranged in a separate list, in addition to being inserted into the event list, for the convenience of the user. For example, EKG data can be separately stored so that the user can generate a histogram of the EKG beats.

As shown in FIG. 3, the global event collector 300 distributes the event list with the event data to data collect servers 310 for eventual processing by the pairing servers 330. In one embodiment, data is periodically transferred to the pairing servers when either a given amount of time or number of events is reached. Data transfer to the pairing servers is performed by periodically packing portions of the event list, which are compiled in the temporary buffer of the global event collector, into messages and transmitting them to the servers. For optimal data transfer, the size and rate of the messages are functions of the event count rate. At higher count rates, the messages become larger, thus the overhead associated with each message becomes negligible. At lower count rates, the message overhead is much less important, because of the abundance of available bandwidth, hence smaller messages are sent more often to allow the servers to continuously process smaller portions of the data, instead of burst processing of large portions of data and then pausing for long periods.

However efficient the packaging and data transfer of the global event collector, it is finite and it is always possible for the system to be overloaded. It is clear that a combination of event collection activity and imaging can occupy the entire bandwidth and fill up the available temporary memory. The global event collector monitors the speed at which the buffer is being filled and can implement a duty cycle, randomly rejecting events at a rate sufficient to avoid buffer overflow. The rejection of an event would be flagged to the user but, in most cases, is preferable to complete interruption of the data acquisition. The acquisition system also can be configured to allow the duty cycle not to exceed a predetermined limit (e.g., 50%) before the scan is simply aborted due to an excessive count rate. In practice, some of the high activity scans involve short-lived isotopes for which the count rate eventually goes back to an acceptable level making the salvaging of the scan (by not completely interrupting the acquisition) even more valuable.

Figure 1:
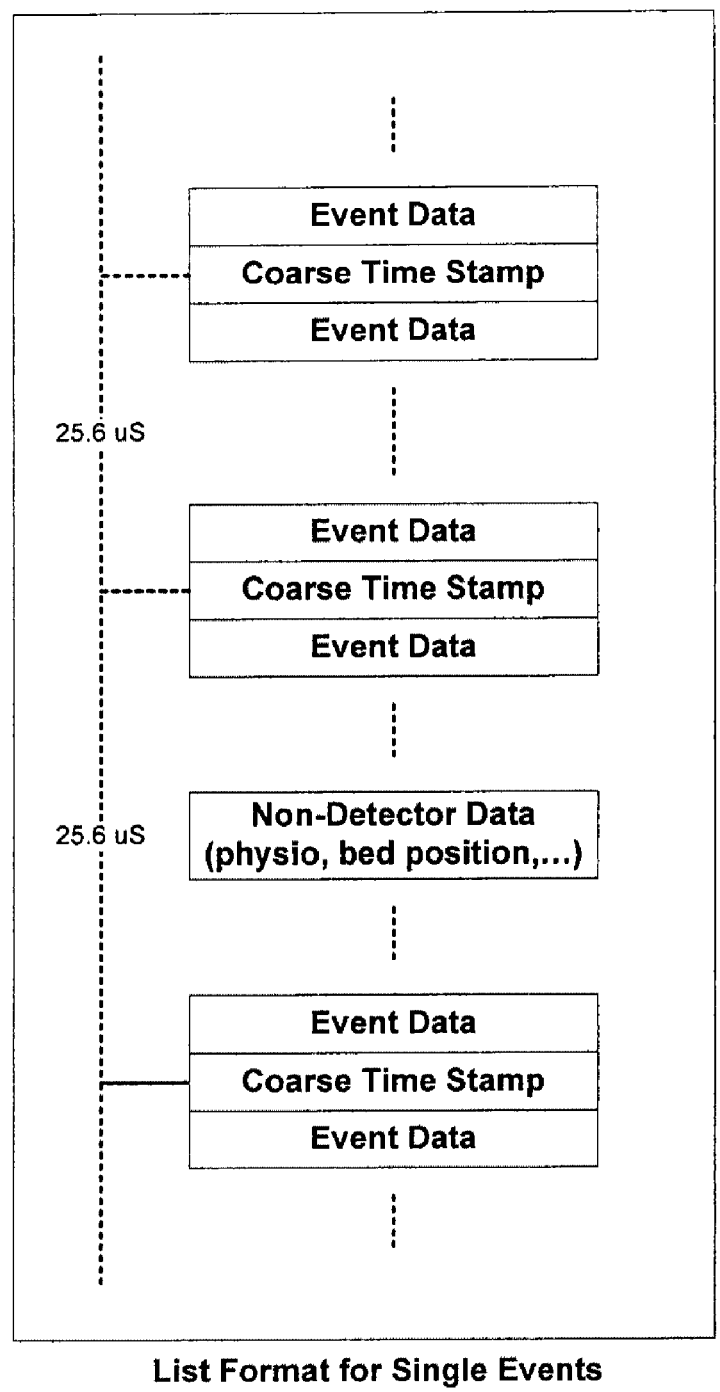
FIG. 1 illustrates a list format for single events.

FIG. 1 illustrates a format of the above-mentioned event list used in an exemplary embodiment of the present invention. As shown in FIG. 1, the event list contains a sequence of entries. Each entry contains an "Entry Type" field to indicate the type of data included in the entry. For single events, at least three different entry types are used: (1) event data; (2) coarse time stamp data; and (3) non-event data, such as physiological data, bed position, detector position, EKG data, etc. As shown in FIG. 1, in one embodiment, a coarse time stamp event occurs every 25.6 microseconds. Non-detector events will typically occur much less frequently than the event data of coarse time stamp events.

As shown in FIG. 2, in one embodiment, a format of an event data entry includes four fields: (1) a 9-bit energy field; (2) an 18-bit crystal position field; (3) a 20-bit fine stamp; and (4) an entry type field. The energy field specifies the energy of the detected event, while the crystal position field identifies the crystal location of the event. In one embodiment, the fine time stamp has a resolution of 24.4 ps, and thus a range of 25.6 µs.

As shown in FIG. 2, in one embodiment, the coarse time stamp field includes: (1) a 32-bit coarse time field, and (2) an entry type field. The resolution of the coarse time stamp field is equal to the range of the fine time stamp field, i.e., in one embodiment 25.6 µs. Accordingly, since 32 bits are allocated to the coarse time stamp field, the range is approximately 30 hours in this embodiment.

Field types and the allocations of bits to each field, other than those described above, can also be used.

FIG. 2 also illustrates a global time stamp that can be derived from each event in the list by concatenating the coarse time stamp and the fine time stamp to provide a resolution of 24.4 ps and a range of approximately 30 hours.

As described above, the global event collector is primarily responsible for generating the event list shown in FIG. 1 and transmitting the event data to the data collect servers and the pairing servers for processing (i.e., event pairing and reconstruction). However, depending on the availability of resources, which depends on event count rates, the global event collector can also perform data processing tasks including filtering, event pairing, and reconstruction.

In one embodiment, the global event collector 300 is implemented in programmable logic, which allows it to be reconfigured to perform different functions on the fly. For example, during a PET scan, the initial count rates are typically very high and most of the logic resources of the global event collector will be utilized to transfer the event data in the event list to the data collect servers. As the scan continues, the count rates will decrease, which will allow some of the logic of the global event collector to be freed up for data processing. As count rates continue to further decrease, more and more of the logic resources of the global event collector can be dedicated to data processing, assisting the efforts of the pairing server.

Thus, the global event collector constantly monitors count rates and decides whether to perform data processing, thus fully utilizing the system's resources, which results in a cost-effective system and faster image processing. The count rate is continuously being monitored by each detector module, but all detector modules provide this information to the global event collector and the global event collector computes the real time count rate for the entire PET scanner. Based on the count rate for the entire scanner, the global event collector decides what kind and amount of data processing it can perform, in addition to data acquisition, at any given time. Thus, it is possible to adjust how the different computing resources are allocated dynamically, according to the instantaneous count rate within a study. For example, in an Rb86 study, an extreme count rate lasts for the first minute or two and then progressives into a medium or low count rate.

Figure 4:
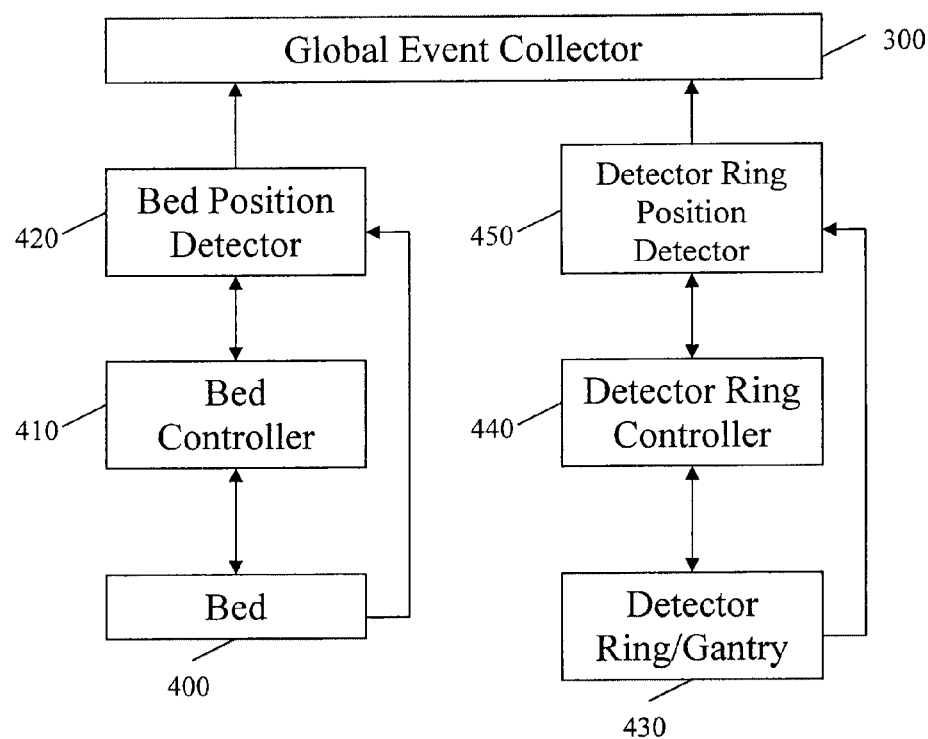
FIG. 4 is a system diagram illustrating the collection of non-detector events.
Figure 5:
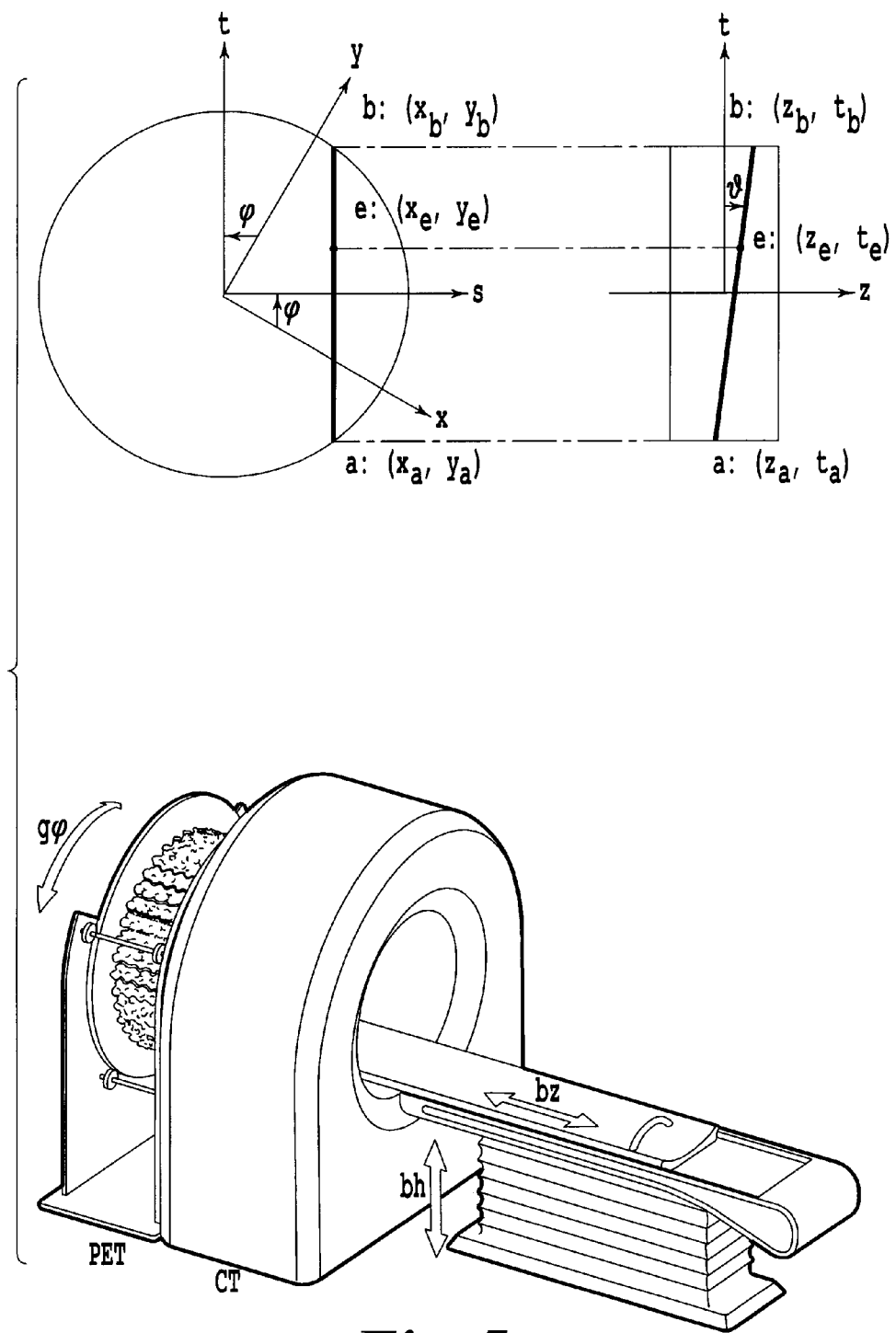
FIG. 5 is a diagram illustrating a PET/CT scanner and associated coordinate system.

FIG. 4 illustrates a portion of the PET system in which non-detector events, including the position of the bed and the position of the detector ring/gantry, are detected and sent to the global event collector 300 shown in FIG. 3. See also FIG. 5. As shown in FIG. 4, the position of a patient bed 400 is controlled by a bed controller 410. The bed controller controls the bed based on a scan trajetory that can be set by an operator. Similarly, the position and/or rotation of the detector ring/gantry 430 is controlled by the detector ring controller 440. The detector ring controller controls the detector ring based on a scan trajectory that can be set by an operator. In an alternative embodiment the bed controller and the scan controller can be integrated into a single control unit that controls both the patient bed and the detector ring based on predetermined or operator-selected scan trajectories. The bed controller 410 and the detector ring controller 440 can be implemented in hardware or in a hardware/software combination.

The bed position detector 420 periodically detects the position and/or velocity of the patient bed 400 and sends the detected position to the global event collector 300 as a non-detector event. The bed position detector includes various sensors for detecting movement of the patient bed 400. Similarly, the detector ring position detector 450 periodically detects the position and/or angular velocity of the detector ring 430 and sends the detected position to the global event collector 300 as a non-detector event. The detector ring position detector includes various sensors for detecting movement of the detector ring 430.

Figure 6:
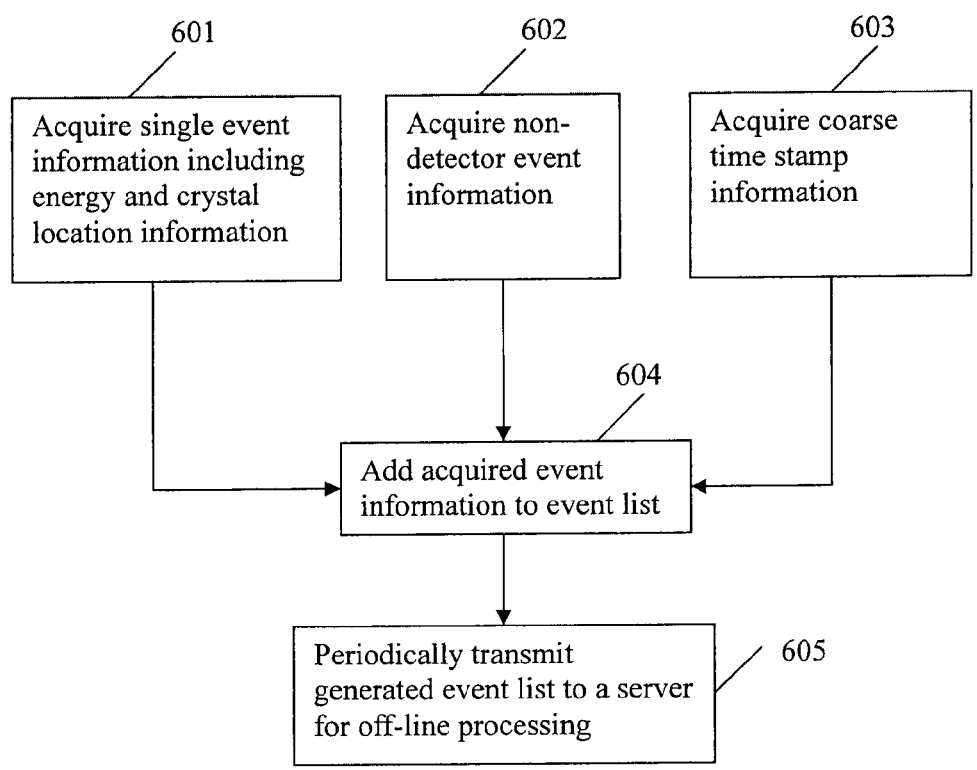
FIG. 6 is a flowchart of a method according to an embodiment of the present invention.

FIG. 6 is a flowchart of a method according to an embodiment of the present invention. In FIG. 6, steps 601-603 are performed continuously and simultaneously. In step 601 single PET annihilation events are detected by the detector modules in the detector ring. In step 601, an event will include, for example, the crystal location and energy of the event. In step 602, non-detector event information related to the position of the patient bed, detector ring, etc. is detected. For example, a change in the position of the bed is a non-detector event that is acquired in step 602. In step 603, coarse time stamp information is periodically obtained. In step 604, the acquired PET detector events, the acquired non-detector events, and the coarse time stamps are added to an event list as they occur. It will be appreciated that the PET detector events and non-detector events will occur at different frequencies and will be added to the event list accordingly. In step 605, the event list, or portions thereof, are transmitted to a pairing server or other computer for off-line processing, e.g., list-mode reconstruction. Step 605 may be performed periodically or based on the size of the event list.

In the context of this invention, the term "off-line" refers to a system that can process events at a time significantly different than the time during which they were detected. In a practical implementation, it is of course desirable to initiate the pairing operation as quickly as possible after detection so as to obtain an image in an acceptable period of time. In an alternate implementation, the detection and pairing occurs at the same time (on different events) in a pipeline mode.

An advantage of embodiments of the present invention is that the system automatically scales with any number of independent detector elements, provided that each element is synchronized and the data is sent in a common format on the communication line. In this regard, it is assumed that the communication line has enough bandwidth to accommodate all the events to the processing servers, and that the processing servers are powerful enough to process the all the incoming events.

Another advantage of embodiments of the present invention is that, if either the communication line or the processing unit is not be powerful enough to process all the incoming events, buffers at the detector and/or at the processing unit can temporarily "hold" the information and send it for processing when bandwidth and/or processing time is available. This is typically the case for short-lived isotopes where intense bursts of activity at the very beginning of the study are followed by lower and lower rates as the physical and biological distribution of the radiotracers decreases. A very typical case of this situation can be seen in a first-pass rubidium study for cardiac perfusion analysis. A larger activity of $^{86}$Rb is injected intravenously in the patient in a substantially bolus mode, all the activity eventually makes it to the heart and is "seen" by the PET detector. As the 90-second half-life rubidium decays and the activity is more and more evenly distributed over the entire body, the count rate also drastically decreases.

A further advantage of embodiments of the present invention is that the system allows the same data to be processed within two or more coincidence windows. Since the data is stored in an event list, the same data can be processed "off-line" using a variable coincidence window.

Another advantage of embodiments of the present invention is that the system allows for the same coincidence pairing system to be attached to a variety of systems with different number of independent detectors and counting rate capacities. In turn, the coincidence pairing system can easily be scaled to handle a higher expected counting rate by adding processing power to the system.

Various components of the PET system described above, including the global event collector, the data collect servers, and the pairing servers can be implemented using a computer system or programmable logic. A computer system upon which various components of the present invention may be implemented includes a bus or other communication mechanism for communicating information, and a processor coupled with the bus for processing the information. The computer system i also includes a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. The computer system further includes a read only memory (ROM) or other static storage device (e.g., programmable ROM (PROM), erasable PROM (EPROM), and electrically erasable PROM (EEPROM)) coupled to the bus for storing static information and instructions for the processor.

The computer system also includes a disk controller coupled to the bus to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the computer system using an appropriate device interface (e.g., small computer system interface (SCSI), integrated device electronics (IDE), enhanced-IDE (E-IDE), direct memory access (DMA), or ultra-DMA).

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system may also include a display controller coupled to the bus to control a display, such as a cathode ray tube (CRT), for displaying information to a computer user.

The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer system performs a portion or all of the processing steps of the invention in response to the processor executing one or more sequences of one or more instructions contained in a memory, such as the main memory. Such instructions may be read into the main memory from another computer readable medium, such as a hard disk or a removable media drive. One or more processors in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

As stated above, the computer system includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read.

Stored on any one or on a combination of computer readable media, the present invention includes software for controlling the computer system, for driving a device or devices for implementing the invention, and for enabling the computer system to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor for execution. A computer readable medium may take many forms, including but not limited to, non-volatile media, and volatile media. Non-volatile media includes, for example, optical, magnetic disks, and magneto-optical disks, such as the hard disk or the removable media drive. Volatile media includes dynamic memory, such as the main memory.

Various forms of computer readable media may be involved in carrying out one or more sequences of one or more instructions to processor for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system may receive the data on the telephone line and use an infrared transmitter to convert the data to an infrared signal. An infrared detector coupled to the bus can receive the data carried in the infrared signal and place the data on the bus. The bus carries the data to the main memory, from which the processor retrieves and executes the instructions. The instructions received by the main memory may optionally be stored on a storage device either before or after execution by processor.

The computer system also includes a communication interface coupled to the bus. The communication interface provides a two-way data communication coupling to a network link that is connected to, for example, a local area network (LAN), or to another communications network such as the Internet. For example, the communication interface may be a network interface card to attach to any packet switched LAN. As another example, the communication interface may be an asymmetrical digital subscriber line (ADSL) card, an integrated services digital network (ISDN) card or a modem to provide a data communication connection to a corresponding type of communications line. Wireless links may also be implemented. In any such implementation, the communication interface sends and receives electrical, electromagnetic or optical signals that carry digital data streams representing various types of information.

The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). The signals through the various networks and the signals on the network link and through the communication interface, which carry the digital data to and from the computer system, may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system can transmit and receive data, including program code, through the networks, the network link and the communication interface. Moreover, the network link may provide a connection through a LAN to a mobile device such as a personal digital assistant (PDA) laptop computer, or cellular telephone.

Numerous modifications and variations of the present invention are possible in light of the above teachings. It is therefore to be understood that within the scope of the appended claims, the invention may be practiced otherwise than as specifically described herein.

The invention claimed is:

1. A method of processing positron emission tomography (PET) information obtained from a PET detector having a plurality of detector regions, each detector region having at least one detector module and a corresponding regional collector, the method comprising:
- receiving PET event information for a single PET event, the PET event information including energy information and crystal position information of the single PET event;
- receiving non-detector event information;
- generating an event list that includes (1) a single PET event entry, the single PET event entry including a fine time stamp, the energy information, and the crystal position information, and (2) a non-detector event entry that includes the received non-detector event information; and
- transmitting the generated event list to a computer for off-line processing.

2. The method of claim 1, wherein the generating step comprises generating the event list, the event list including coarse time stamp entries at regular, periodic positions within the event list.

3. The method of claim 1, wherein the generating step comprises generating the event list that includes the single PET event entry, the single PET event entry including an entry type.

4. The method of claim 1, wherein the step of receiving the non-detector event information comprises receiving the non-detector event information including at least one of bed location information, angular position of a detector, cardiac EKG information, respiratory gating signal information, events from another detector, and other physiological information.

5. The method of claim 1, further comprising:
- performing, in a pipeline mode, event pairing and reconstruction based on information included in the event list.

6. The method of claim 5, wherein the performing step comprises performing event pairing using at least two different coincidence windows based on the information included in the event list.

7. The method of claim 1, further comprising:
- temporarily storing the received PET event information in a temporary events buffer until availability of communication bandwidth to the computer is available.

8. The method of claim 1, further comprising:
- temporarily storing the transmitted event list in a memory associated with the computer until processing time of the computer is available.

9. The method of claim 1, further comprising:
- temporarily excluding the single PET event from the event list if a condition of memory overflow is detected.

10. The method of claim 1, wherein fine time stamp has a resolution small enough accommodate time-of-flight information.

11. The method of claim 1, wherein the generating stop comprises generating the event list, which includes a plurality of single PET event entries; and
- the transmitting step is performed prior to performing coincidence pairing for the plurality of single PET event entries.

12. A system for collecting and processing positron emission tomography (PET) information, comprising:
- a plurality of detector modules arranged in a plurality of detector regions;
- a plurality of regional event collectors corresponding to the plurality of detector regions, each regional event collector configured to receive PET event information from each detector module in the corresponding detector region; and
- a global event collector configured to receive (1) the PET event information from each of the plurality of regional event collectors, the PET event information including energy information and crystal position information of a single PET event, and (2) non-detector event information, the global event collector further configured to generate an event list that includes (i) a single PET event entry, the single PET event entry including a fine time stamp, the energy information, and the crystal position information, and (ii) a non-detector event entry that includes the received non-detector event information, and to transmit the generated event list to a computer for off-line processing.

13. The system of claim 12, wherein the global event collector is configured to generate the event list, the event list including coarse time stamp entries at regular, periodic positions within the event list.

14. The system of claim 12, wherein the global event collector is configured to generate the event list that includes the single PET event entry, the single PET event entry including an entry type.

15. The system of claim 12, wherein the global event collector is configured to receive the non-detector events information including at least one of bed location information, angular position of a detector, cardiac EKG information, respiratory gating signal information, events from another detector, and other physiological information.

16. The system of claim 12, further comprising:
- the computer configured to receive the event list and to perform, in a pipeline mode, event pairing and reconstruction based on information included in the event list.

17. The system of claim 16, wherein the computer is configured to perform event pairing using at least two different coincidence windows based on the information included in the event list.

18. The system of claim 12, further comprising:
- a temporary events buffer temporarily storing the received PET event information until availability of communication bandwidth to the computer is available.

19. The system of claim 12, further comprising:
- a data collect server configured to temporarily store the transmitted event list until processing time of the computer is available.

20. The system of claim 12, wherein the global event collector is configured to temporarily exclude the single PET event from the event list if a condition of memory overflow is detected.

21. A computer-readable medium storing a computer program that when executed by a computer, causes the computer to perform a method of processing positron emission tomography (PET) information obtained from a PET detector having a plurality of detector regions, each detector region having at least one detector module and a corresponding regional collector, the method comprising:
- receiving PET event information for a single PET event, the PET event information including energy information and crystal position information of the single PET event;
- receiving non-detector event information;
- generating an event list that includes (1) a single PET event entry, the single PET event entry including a fine time stamp, the energy information, and the crystal position information, and (2) a non-detector event entry that includes the received non-detector event information; and
- transmitting the generated event list to a computer for off-line processing.

* * * * *